United States Patent [19]
Ahlert

[11] Patent Number: 5,593,453
[45] Date of Patent: Jan. 14, 1997

[54] PROSTHESIS COVER

[76] Inventor: Gary Ahlert, 135½ Dearborn Ave., Rye, N.Y. 10580

[21] Appl. No.: 426,227

[22] Filed: Apr. 21, 1995

[51] Int. Cl.⁶ .................................................. A61F 2/78
[52] U.S. Cl. .................. 623/27; 2/270; 36/138; 602/3
[58] Field of Search ................... 602/3, 62, 77, 602/63, 65; 2/22, 270, 911, DIG. 5, 240; 36/103, 109, 70 R, 138; 623/27

[56] References Cited

U.S. PATENT DOCUMENTS

| | | | |
|---|---|---|---|
| 377,203 | 1/1888 | Langen | 36/109 |
| 384,155 | 6/1888 | Hathorn | 36/138 X |
| 2,244,871 | 6/1941 | Guinzburg | 2/22 X |
| 3,590,390 | 7/1971 | Howard et al. | 2/240 X |
| 3,802,424 | 4/1974 | Newell | 602/3 |
| 3,874,001 | 4/1975 | Patience et al. | 2/240 |
| 3,934,582 | 1/1976 | Gorrie | 602/62 |
| 4,178,924 | 12/1979 | Baxter | 602/3 |
| 4,224,935 | 9/1980 | Metelnick | 602/3 |
| 4,562,834 | 1/1986 | Bates et al. | 602/3 |
| 5,063,919 | 11/1991 | Silverberg | 602/3 |

FOREIGN PATENT DOCUMENTS

| | | | |
|---|---|---|---|
| 0630633 | 12/1994 | European Pat. Off. | 602/63 |
| 2504786 | 11/1982 | France | 36/103 |
| 3902434 | 8/1990 | Germany | 602/63 |
| 0597851 | 4/1978 | Switzerland | 602/62 |
| 0485746 | 5/1938 | United Kingdom | 36/70 R |

*Primary Examiner*—David H. Willse
*Attorney, Agent, or Firm*—Patrick J. Walsh

[57] ABSTRACT

An improved prosthesis cover of waterproof material which closely conforms to the shape of the limb being covered, has an antifriction inner surface and an antiskid sole in the case of a leg cover.

13 Claims, 5 Drawing Sheets

PROSTHESIS COVER

BACKGROUND OF THE INVENTION

The present invention relates to protective covers for prosthetic devices, casts and bandages especially arm and leg prosthesis and cast covers for protecting a prosthesis, cast or bandage when swimming, showering and so forth.

Limbs covered with a bandage or fitted with a cast or prosthetic device should be protected from water and kept dry to avoid deterioration while the wearer showers or swims and so forth.

Prosthetic devices commonly in use as arm and leg replacements simulate the replaced limb to the maximum extent possible including replication of the function, appearance, feel, shape and contour of a normal limb.

Protective covers fabricated of waterproof material such as latex are commonly used as being lightweight, flexible and durable under ordinary usage. Such covers, however, are cumbersome to put on and take off by reason of the tendency of the cast cover to frictionally engage the surface being protected. Accordingly, the present invention provides an improved protective cover for prosthetic devices, casts and bandages that is easier for the user to put on and take off particularly in cases where the replaced or treated limb has the same shape and contour as a normal limb.

SUMMARY OF THE INVENTION

The present invention comprises an improved prosthesis cover preferably fabricated of latex which is form fitting, i.e., closely conforms to the shape of the limb being covered. Each embodiment of the invention is formed to closely fit a prosthetic device as well as a limb in a cast or bandaged limb that very nearly has the size and contour of a normal or healthy limb.

In one embodiment, a prosthetic cover is fitted with finger grips to aid the user in applying and removing the cover by sliding the cover into place, and includes antifriction means on the inner surface to reduce frictional contact between the cover and the prosthetic device, cast or bandage being protected.

In another embodiment, the prosthesis cover is preferably formed of latex with a relatively thin covering wall to allow rolling up and down of the cover when being applied or removed from a limb. This embodiment also includes antifriction means on the inner surface to reduce frictional contact between the cover and the prosthetic device, cast or bandage being protected.

The prosthesis cover when used as a leg cover is provided with an antiskid sole to prevent slipping on wet surfaces as in showers or in the vicinity of swimming pools.

In a preferred embodiment of the invention, a prosthesis cover is in the form of a leg boot for covering the leg up to the knee. The cover is preferably provided with finger grips on both sides near the top or open end, and at the back of the heel. These grips, which may be in the form of integrally molded loops, enable the user to readily apply and remove the cover. In addition, the cover is provided along its interior surface with a plurality of inwardly directed, prosthesis engaging ribs for spacing the inner cover surface from the prosthesis thereby to reduce frictional engagement between inner surface and prosthesis. At the same time the ribs engage the prosthesis and prevent the prosthesis from slipping down along the leg during use.

The leg boot is further provided with a molded integral antiskid sole of robust construction to allow repeated use of the cover in walking about, while protecting against accidental slipping especially on wet surfaces.

OBJECTS OF THE INVENTION

It is an object of the invention to provide an improved cover for prosthetic devices, casts and bandages.

It is an object of the invention to provide a protective cover for limbs which is easy to apply and remove.

It is an object of the invention to provide a protective cover for limbs which is easy to apply and remove particularly in cases where the limb has the shape and contour of a normal or healthy limb.

It is a further object of the invention to provide a prosthesis cover having exterior gripping means to enable the user to apply and remove the cover.

It is a further object of the invention to provide a prosthesis cover with an antifriction inner surface as an aid in ease of applying and removing a cover, while retaining effective engagement of cover and prosthesis to prevent slipping of the cover from the prosthesis.

It is a further object of the invention to provide a prosthesis cover in the form of a leg boot with a molded antifriction sole to reduce the hazard of slipping on wet surfaces.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which.

DETAILED DESCRIPTION OF THE INVENTION

Figure 1:
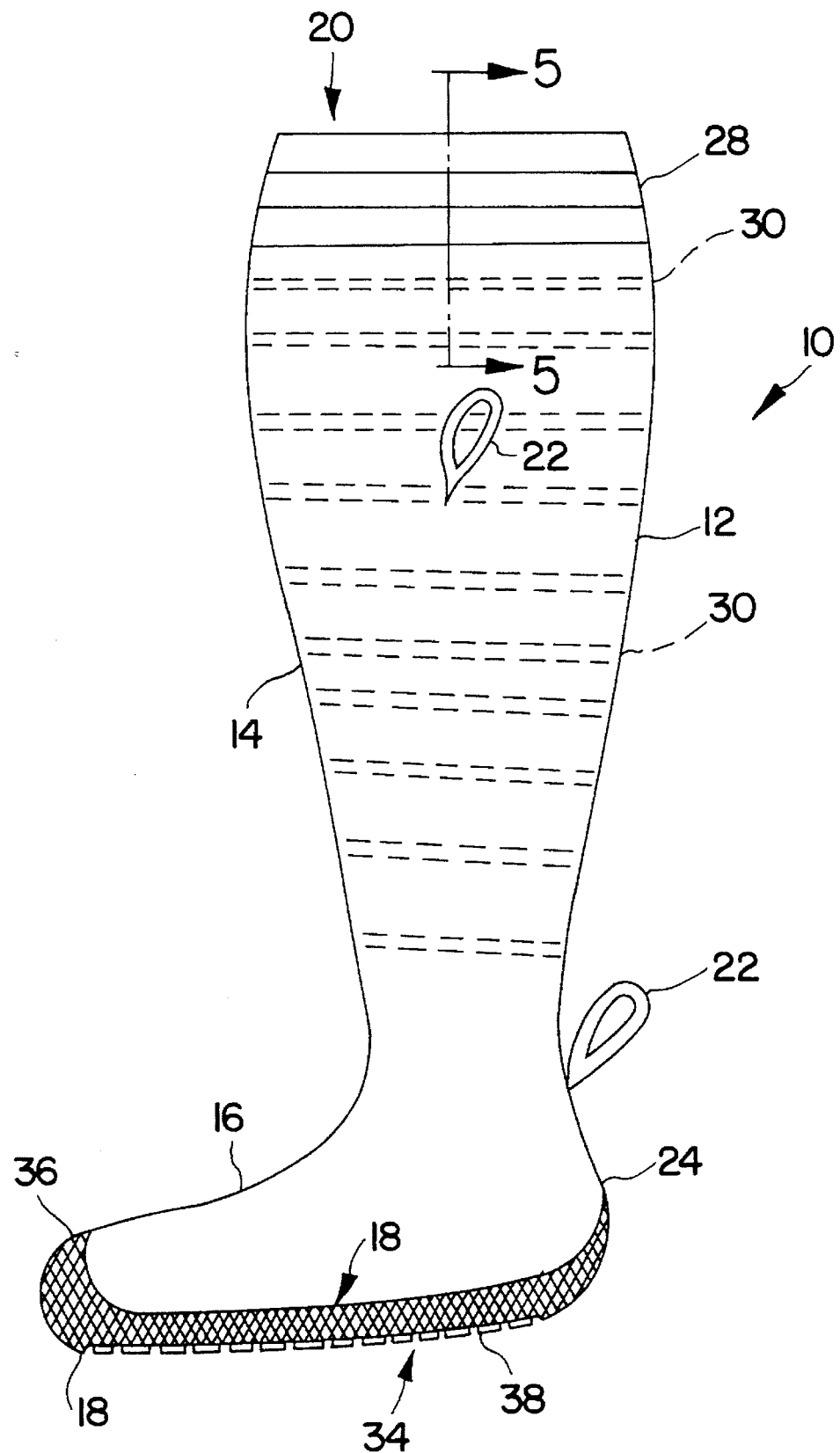
FIG. 1 is a side elevation of a prosthesis cover according to the invention.
Figure 2:
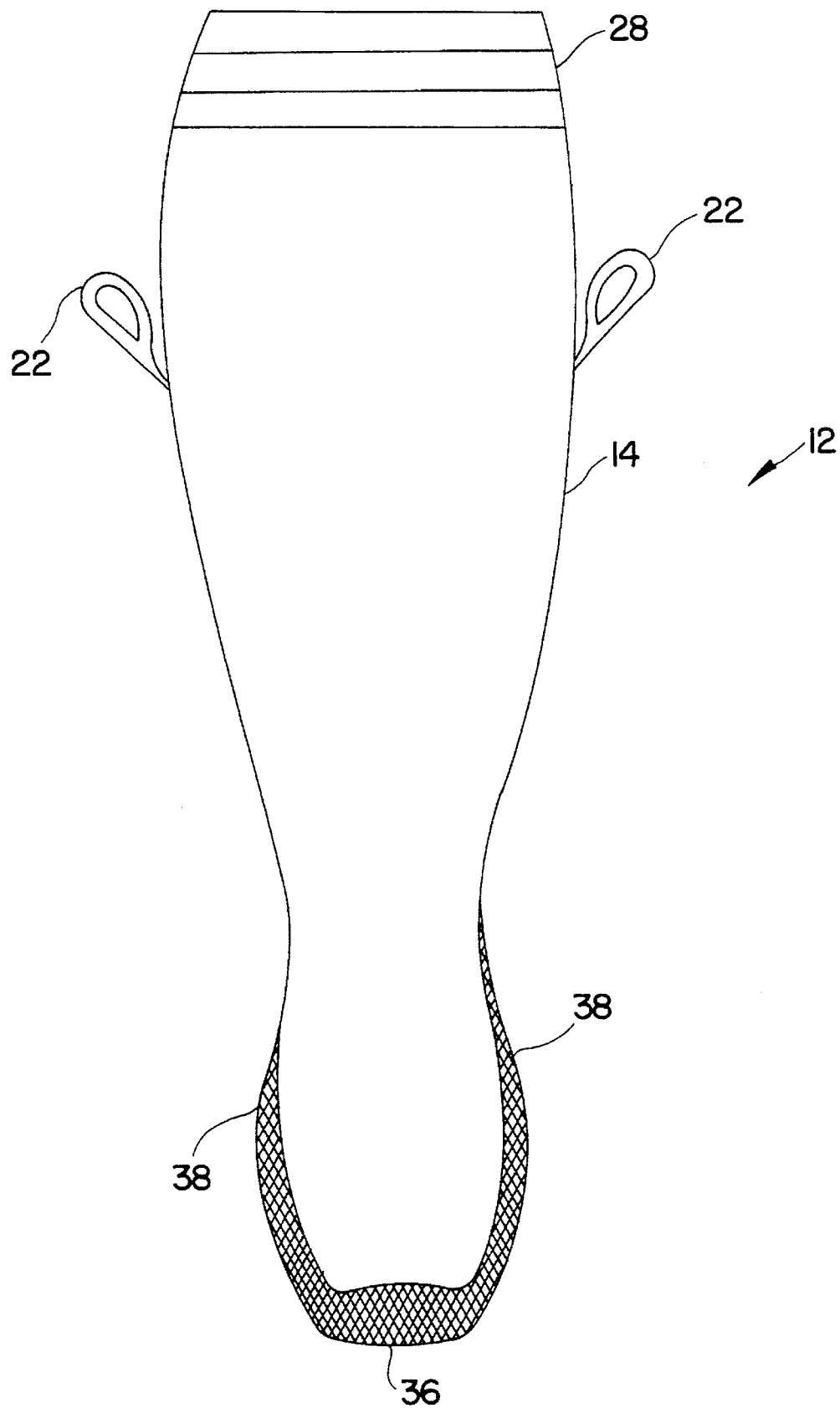
FIG. 2 is a front elevation view thereof.
Figure 3:
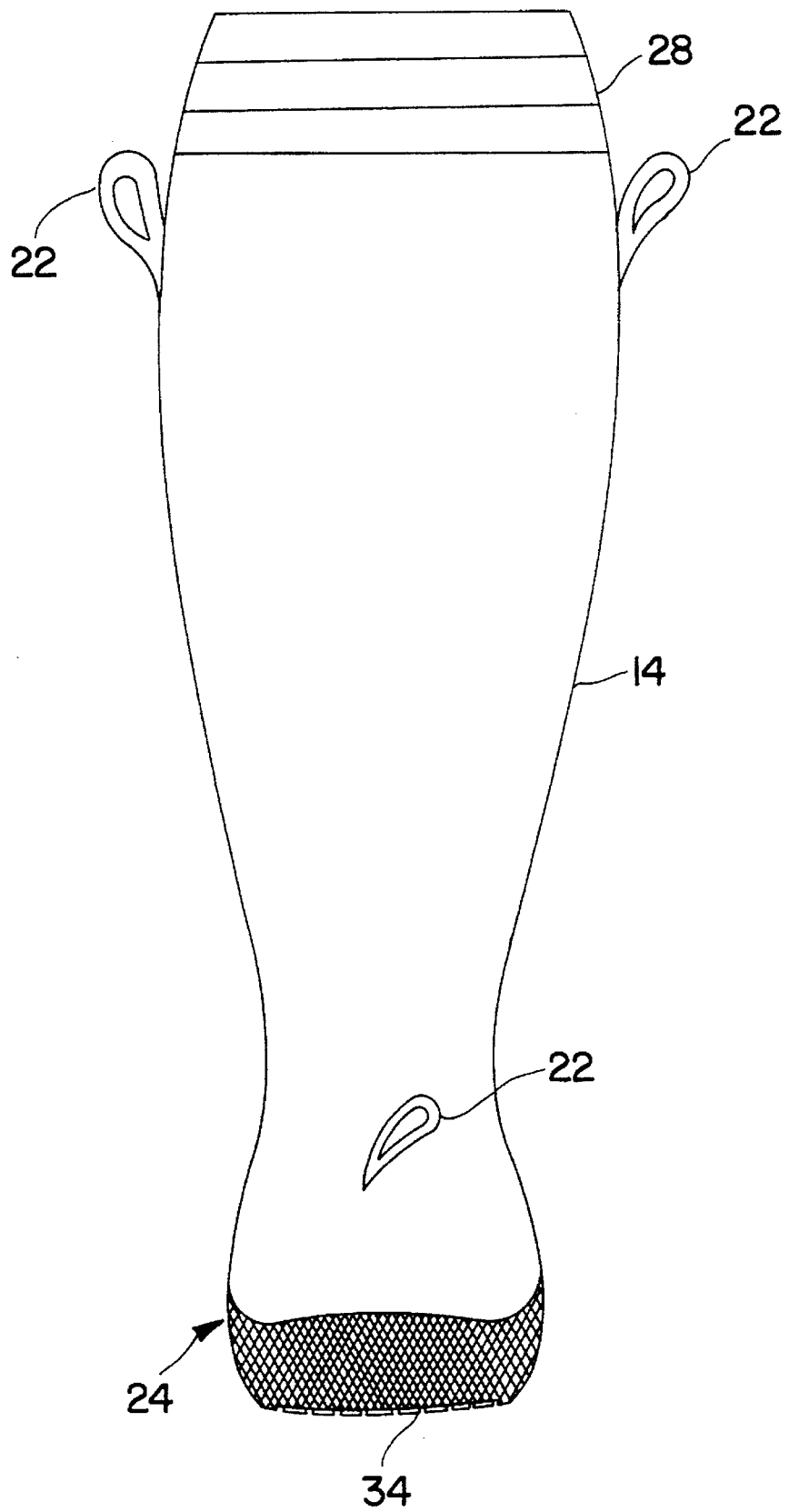
FIG. 3 is a rear elevation view thereof.
Figure 4:
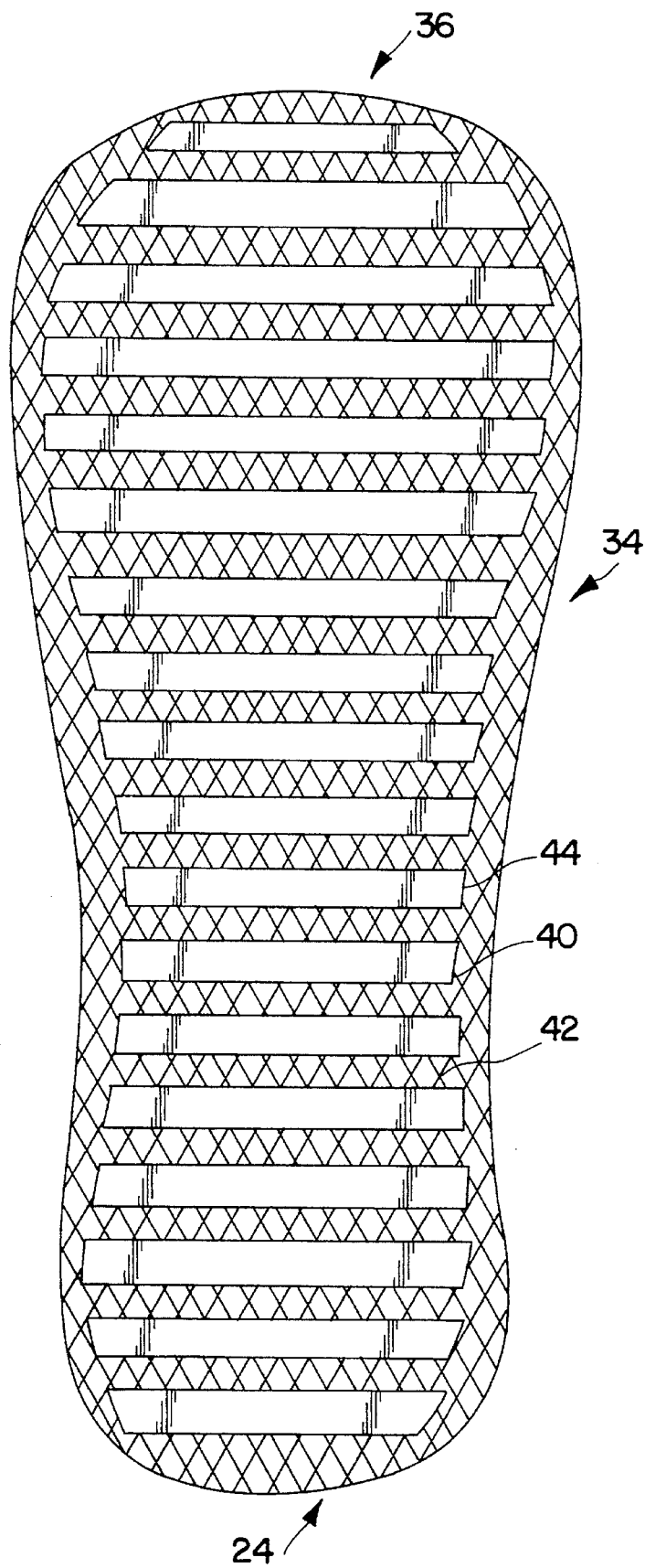
FIG. 4 is a bottom view thereof.

Referring now to the drawing, a preferred embodiment of prosthesis cover 10 according to the invention is in the form of a leg boot 12 preferably fabricated of latex or similar waterproof film material. The boot is preferably formed in one piece and includes leg 14 and foot 16 portions, an integral sole 18, an open top end 20, and finger loops or grips 22 positioned behind the heel 24 and on opposite sides of the leg portion just below the open top.

Figure 5:
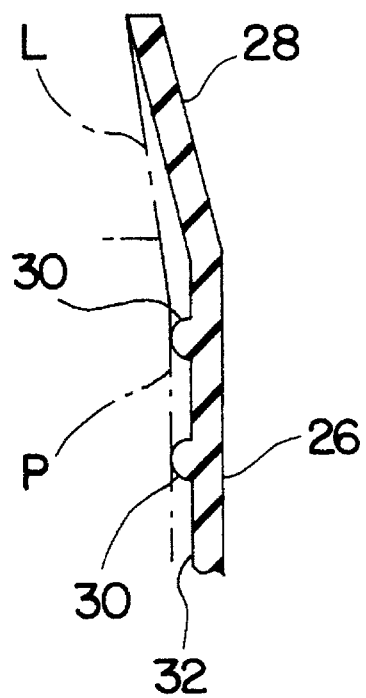
FIG. 5 is a section view taken along line 5—5 of FIG. 1.

The leg portion of this embodiment of the boot preferably has a wall 26 thickness of at least 0.005 inches and is permanently shaped to closely conform to the contour of a normal limb. The top segment 28 of the leg portion, as best shown in FIG. 5, is from 1 to 3 inches high and is frusto-conical in shape tapering inwardly from the vertical a distance of ¼" to ¾". The inward taper provides for frictional engagement of the top segment with the prosthetic device P, cast or bandage, or indeed with a section of healthy limb L adjacent the prosthetic device, cast or bandage.

As shown in FIG. 5, inwardly directed ribs 30 are formed on the inner surface 32 of the leg portion of the cover for spacing the inner cover surface from a prosthesis cast or bandage thereby to reduce frictional engagement particularly when the cover is being applied by sliding over the prosthesis. When the cover is in place, the ribs 30 engage the prosthesis and prevent the prosthesis cover from slipping down along the leg during use, particularly when the user engages in physical activity such as swimming and so forth. The plurality of ribs are spaced one to several inches apart, extend concentrically of the leg portion from just above the ankle portion throughout the height of the leg portion to just below the top segment for providing the desired antifriction result. Rib thickness is approximately the same as the wall thickness of the leg portion.

As an additional aid to applying the cover, the inner surface 32 may be coated with a suitable antislip powder such as talc, or liquid such as silicone.

The leg boot is further provided with a molded integral antiskid surface 34 of robust construction to allow repeated use of the cover in walking about, while protecting the wearer against accidental slipping especially on wet surfaces, and while protecting a prosthesis from scuffing or abrasion. The antiskid surface covers the bottom or sole 18 of the leg boot as well as the toe portion 36, the heel portion 24 and side marginal edges 38 between the toe and heel on both sides of the boot. The antiskid surface is characterized by a pattern of projections 40 and depressions 42 in the surface contour having the general appearance of a knurl which produce the desired antiskid property.

The antiskid surface of the sole includes a plurality of spaced upstanding cross bars 44 each extending substantially the full width of the sole between toe and sole. The plurality of cross bars constitute a ground engaging tread with an antiskid characteristic to prevent slipping on wet surfaces in lavatories, swimming areas and so forth. In a preferred embodiment, the antiskid surface cross bars are ⅛ to ¼ inches long (measured in toe-to-heel direction) and in the aggregate cover approximately 40% to 60% of the surface of the sole.

The sole including the antiskid surface may be formed integral of the same material, latex for example, with the remainder of the cover. Alternately, the sole can be formed separately of rubber or synthetics such as a copolymer of styrene and butadiene with high friction characteristics and assembled to the leg portion with a suitable adhesive for example.

Finger loops or grips 22 are affixed to the cover behind the heel and on opposite sides of the leg portion just below the open top as a aid in applying and removing the cover. The finger loops can be molded integral in the cover, or can be assembled with use of suitable adhesives.

Figure 6:
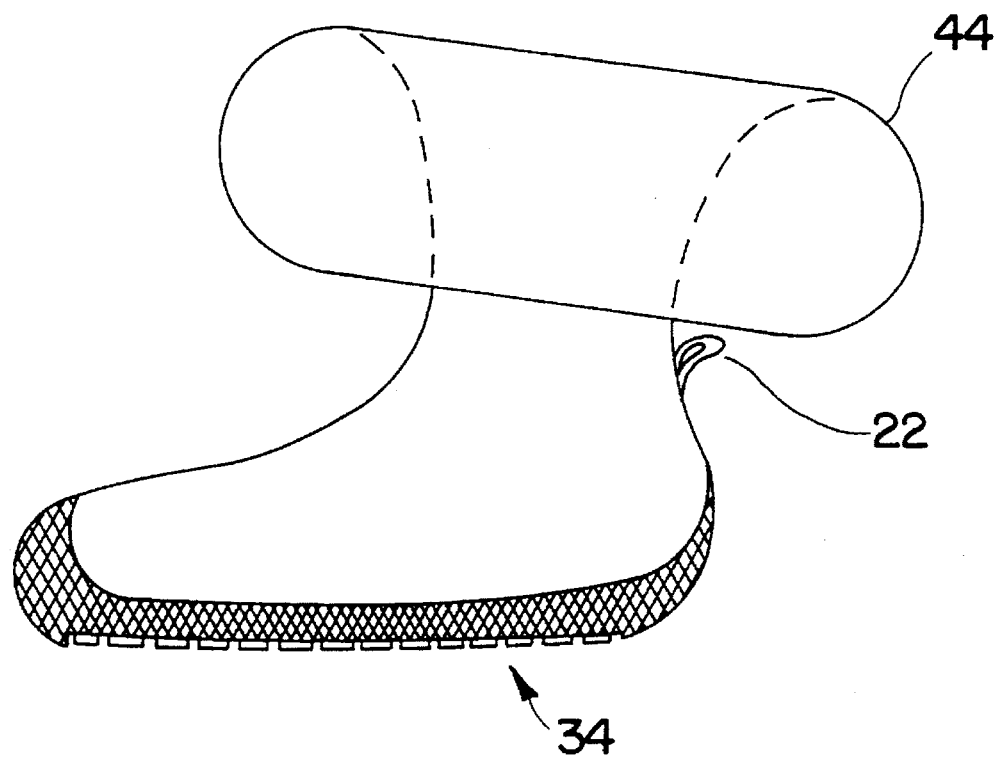
FIG. 6 is a side elevational view of a modified embodiment of the invention showing a prosthetic cover in rolled down position prior to being applied to a limb.

A modified embodiment of the invention is illustrated in FIG. 6 in which the thickness of the leg portion wall 44 is from 0.002 to 0.005 inches to allow rolling of the leg portion for the purpose of applying or removing the cover from a prosthesis. The cover may be packaged as shown in FIG. 6 for ease of application and to acquaint the user with correct technique for applying and removing the cover.

The modified embodiment is also provided with concentric antifriction ribs 30 throughout the leg portion, an antiskid 34 sole construction, and inner surface powder or liquid slip agent as the preferred embodiment of FIGS. 1–5.

I claim:

1. A prosthesis cover formed of waterproof sheet material having leg and foot portions, the foot portion having sole, toe and heel portions and side marginal edges between the toe and sole on both sides of the cover, an antiskid surface covering the foot portion, an open top end, the leg portion having a frusto-conical top segment for engagement with the prosthesis at the top end of the cover, finger loops positioned behind the heel and on opposite sides of the leg portion just below the open top, the leg and foot portions having contours and shape closely conforming to the shape of the prosthesis being covered, and a plurality of inwardly directed ribs being formed on the inner surface of the leg portion of the cover, the plurality of ribs being spaced apart from each other with each rib extending concentrically of the leg portion, the plurality of ribs extending along said inner surface from just above an ankle portion throughout the height of the leg portion to just below the top segment, so that the plurality of ribs spaces the inner cover surface from the prosthesis thereby to reduce frictional engagement when the cover is being applied by sliding over the prosthesis, and so that when the cover is in place the ribs engage the prosthesis and prevent the cover from slipping down along the prosthesis during use.

2. A prosthesis cover as defined in claim 1 which is fabricated of latex.

3. A prosthesis cover as defined in claim 1 which is fabricated of waterproof sheet material.

4. A prosthesis cover as defined in claim 1 in which the leg portion has a wall thickness of at least 0.005 inches and is permanently shaped to closely conform to the contour of a normal limb.

5. A prosthesis cover as defined in claim 4 in which a rib thickness is the same as the wall thickness.

6. A prosthesis cover as defined in claim 1 in which the top segment of the leg portion is from 1 to 3 inches high and is frusto-conical in shape tapering inwardly from the vertical a distance of ¼" to ¾".

7. A prosthesis cover as defined in claim 1 in which the plurality of ribs are spaced one to several inches apart, with a rib thickness being approximately the same as a wall thickness of the leg portion.

8. A prosthesis cover as defined in claim 1 in which the foot portion includes an antiskid surface of robust construction to allow repeated use of the cover in walking about, the antiskid surface covering the sole, toe, heel portions of the cover, and the side marginal edges between the toe and heel on both sides of the cover, the antiskid surface being characterized by a pattern of projections and depressions in the surface contour having the general appearance of a knurl which produce the desired antiskid property, the antiskid surface of the sole further including a plurality of spaced upstanding cross bars each extending substantially the full width of the sole between toe and sole, the plurality of cross bars constituting a ground engaging tread with an antiskid characteristic to prevent slipping on wet surfaces.

9. A prosthesis cover as defined in claim 8 in which the antiskid surface cross bars are ⅛ to ¼ inches long and in the aggregate cover approximately 40% to 60% of the surface of the sole.

10. A prosthesis cover as defined in claim 8 in which the antiskid surface is formed of a copolymer of styrene and butadiene with high friction characteristics.

11. A prosthesis cover as defined in claim 1 in which the thickness of a leg portion wall is from 0.002 to 0.005 inches so that the leg portion may be rolled and unrolled for the purpose of removing or applying, respectively, the cover to a prosthesis.

12. A prosthesis cover as defined in claim 1 in which the inner surface is coated with an antislip powder.

13. A prosthesis cover as defined in claim 1 in which the inner surface is coated with an antislip liquid.

* * * * *